US008821472B2

(12) United States Patent
Sparholt et al.

(10) Patent No.: US 8,821,472 B2
(45) Date of Patent: Sep. 2, 2014

(54) RESERVOIR DEVICE WITH INTEGRATED MOUNTING MEANS

(75) Inventors: Philip Albert Sparholt, Smoerum (DK); Erik Winkel Ethelfeld, Copenhagen K (DK); Steffan Hansen, Hilleroed (DK); Bjorn G. Larsen, Birkeroed (DK); Claus S. Moeller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/407,490

(22) Filed: Apr. 20, 2006

(65) Prior Publication Data
US 2007/0066955 A1    Mar. 22, 2007

Related U.S. Application Data

(63) Continuation of application No. PCT/DK2004/000725, filed on Oct. 21, 2004.

(60) Provisional application No. 60/518,881, filed on Nov. 10, 2003, provisional application No. 60/518,832, filed on Nov. 10, 2003.

(30) Foreign Application Priority Data

Oct. 21, 2003  (DK) ................................ 2003 01545
Oct. 23, 2003  (EP) ..................................... 03024276
Oct. 28, 2003  (DK) ................................ 2003 01590

(51) Int. Cl.
| | |
|---|---|
| *A61J 1/10* | (2006.01) |
| *A61J 1/14* | (2006.01) |
| *A61J 1/16* | (2006.01) |
| *A61M 5/142* | (2006.01) |

(52) U.S. Cl.
CPC *A61J 1/1406* (2013.01); *A61J 1/10* (2013.01); *A61J 1/1475* (2013.01); *A61J 1/16* (2013.01); *A61J 1/1462* (2013.01); *A61M 5/14276* (2013.01); *A61M 2005/14252* (2013.01); *B65D 2583/005* (2013.01)
USPC .............. 604/415; 604/48; 604/403; 604/408; 604/411; 222/92; 222/563

(58) Field of Classification Search
CPC ......... A61J 1/10; A61J 1/1406; A61J 1/1475; A61J 1/16; A61J 1/1462; A61M 5/14276; A61M 2005/14252; A61M 5/1428; A61M 5/14248; A61M 5/14216; B65D 75/008; B65D 2583/005
USPC ...... 128/DIG. 12, DIG. 13; 604/48, 500, 506, 604/513, 519, 520, 415, 19, 27, 28, 93.01, 604/95.01, 131, 140, 146, 152, 153, 154, 604/403, 404, 407, 408, 411
See application file for complete search history.

(56) References Cited

U.S. PATENT DOCUMENTS

| | | | |
|---|---|---|---|
| 2,704,075 | A | 3/1955 | Cherkin |
| 2,856,929 | A | 10/1958 | Gossett et al. |

(Continued)

FOREIGN PATENT DOCUMENTS

| | | |
|---|---|---|
| CH | 337990 | 4/1955 |
| DE | 2160939 | 6/1973 |

(Continued)

OTHER PUBLICATIONS

U.S. Appl. No. 11/407,608 to Sparholt et al, Dec. 12, 2007.*
Non-Final Office Action mailed May 18, 2008, in U.S. Appl. No. 11/407,608, which was filed Apr. 20, 2006 by Sparholt et al.
Response and Amendment (including most recent claims) submitted Aug. 13, 2008, in U.S. Appl. No. 11/407,608.

(Continued)

*Primary Examiner* — Adam Marcetich
(74) *Attorney, Agent, or Firm* — Wesley A. Nicolas; Reza Green; Richard W. Bork

(57) ABSTRACT

The present invention provides an apparatus comprising a housing and a flexible reservoir adapted to contain a fluid and having a septum member formed from a needle-penetratable self-sealing material. The flexible reservoir is arranged within the housing in combination with mounting means arranged within or formed by the housing, wherein the mounting means engages the septum member to thereby mount the flexible reservoir relative to the housing. In this way a secure fixation between the reservoir and the housing is provided without having to interfere with the general flexibility of the reservoir, e.g. substantially the entire flexible reservoir apart from the outlet/mounting means may be arranged free to move relative to the housing, this allowing the reservoir to be emptied to a high degree.

9 Claims, 8 Drawing Sheets

(56) References Cited

U.S. PATENT DOCUMENTS

| | | | |
|---|---|---|---|
| 3,108,732 A * | 10/1963 | Curie et. al. | 229/117.3 |
| 3,161,310 A | 12/1964 | Barton et al. | |
| 3,642,047 A | 2/1972 | Waage | |
| 4,257,535 A * | 3/1981 | Mellett | 222/92 |
| 4,274,407 A * | 6/1981 | Scarlett | 604/153 |
| 4,326,574 A | 4/1982 | Pallaroni et al. | |
| 4,362,158 A | 12/1982 | Lena | |
| 4,362,255 A * | 12/1982 | Bond | 222/107 |
| 4,416,595 A * | 11/1983 | Cromie | 417/476 |
| 4,516,977 A | 5/1985 | Herbert | |
| 4,551,138 A | 11/1985 | Shinohara | |
| 4,553,693 A | 11/1985 | Terajima et al. | |
| 4,553,971 A * | 11/1985 | Ashley et al. | 604/415 |
| 4,632,673 A | 12/1986 | Tiitola et al. | |
| 4,645,486 A | 2/1987 | Beal et al. | |
| 4,801,777 A * | 1/1989 | Auerbach | 219/687 |
| 4,814,794 A * | 3/1989 | Sato | 347/28 |
| 4,886,499 A | 12/1989 | Cirelli et al. | |
| 5,006,117 A | 4/1991 | Cassou | |
| 5,041,517 A | 8/1991 | Vu et al. | |
| D338,726 S * | 8/1993 | Andersen et al. | D24/118 |
| 5,248,300 A * | 9/1993 | Bryant et al. | 604/134 |
| 5,307,955 A * | 5/1994 | Viegas | 222/107 |
| 5,330,431 A * | 7/1994 | Herskowitz | 604/153 |
| 5,348,539 A * | 9/1994 | Herskowitz | 604/141 |
| D361,838 S * | 8/1995 | Kuhn et al. | D24/118 |
| 5,480,067 A * | 1/1996 | Sedlmeier | 222/107 |
| 5,480,386 A * | 1/1996 | Brohy et al. | 604/131 |
| 5,514,123 A * | 5/1996 | Adolf et al. | 604/411 |
| 5,666,146 A * | 9/1997 | Mochizuki et al. | 347/86 |
| 5,681,284 A * | 10/1997 | Herskowitz | 604/141 |
| 5,734,401 A * | 3/1998 | Clark et al. | 347/86 |
| 5,772,607 A | 6/1998 | Magram | |
| 5,833,368 A | 11/1998 | Kaufman | |
| 5,873,656 A * | 2/1999 | Arkins et al. | 383/202 |
| 5,891,096 A * | 4/1999 | Hyun et al. | 604/131 |
| 5,950,403 A | 9/1999 | Yamaguchi et al. | |
| 5,957,895 A * | 9/1999 | Sage et al. | 604/181 |
| 5,960,993 A * | 10/1999 | Mitsui et al. | 222/92 |
| 5,971,533 A * | 10/1999 | Kinoshita et al. | 347/86 |
| 5,997,177 A * | 12/1999 | Kaufman | 383/5 |
| 6,074,369 A * | 6/2000 | Sage et al. | 604/181 |
| 6,079,594 A * | 6/2000 | Brown et al. | 222/107 |
| 6,116,782 A | 9/2000 | Arkins et al. | |
| 6,210,391 B1 * | 4/2001 | Lord | 604/403 |
| 6,270,255 B1 | 8/2001 | Kaufman et al. | 383/5 |
| 6,302,300 B1 * | 10/2001 | Bosch | 222/107 |
| 6,322,739 B1 | 11/2001 | Andersson et al. | |
| 6,382,441 B1 | 5/2002 | Carano | |
| 6,394,993 B1 * | 5/2002 | Chang et al. | 604/415 |
| 6,406,458 B1 * | 6/2002 | Tillander | 604/147 |
| 6,414,077 B1 | 7/2002 | Barron et al. | |
| 6,419,393 B1 * | 7/2002 | Shibata | 383/202 |
| 6,510,965 B1 * | 1/2003 | Decottignies et al. | 222/95 |
| 6,579,390 B2 | 6/2003 | Tedford, Jr. | |
| 6,592,918 B2 * | 7/2003 | Kaeser | 426/115 |
| 6,613,036 B1 * | 9/2003 | Farmer et al. | 604/408 |
| 6,652,942 B2 * | 11/2003 | Ling et al. | 428/36.91 |
| 6,685,691 B1 * | 2/2004 | Freund et al. | 604/403 |
| 6,786,584 B2 * | 9/2004 | Kaga et al. | 347/86 |
| 7,175,581 B2 | 2/2007 | Murray | |
| 2001/0053891 A1 | 12/2001 | Ackley | |
| 2002/0007155 A1 | 1/2002 | Freund et al. | |
| 2002/0107492 A1 * | 8/2002 | Brach et al. | 604/296 |
| 2002/0123741 A1 * | 9/2002 | Rake et al. | 604/890.1 |
| 2003/0050623 A1 * | 3/2003 | Lord et al. | 604/891.1 |
| 2003/0106902 A1 * | 6/2003 | Bolam | 222/92 |
| 2003/0109827 A1 | 6/2003 | Lavi et al. | |
| 2003/0187423 A1 | 10/2003 | Wilkinson et al. | |
| 2004/0143235 A1 | 7/2004 | Freund et al. | |
| 2005/0150917 A1 * | 7/2005 | Dicks et al. | 222/566 |
| 2006/0036231 A1 | 2/2006 | Conard et al. | |
| 2007/0016159 A1 | 1/2007 | Sparholt et al. | |
| 2007/0066955 A1 | 3/2007 | Sparholt et al. | |
| 2009/0036844 A1 | 2/2009 | Fristrup et al. | |

FOREIGN PATENT DOCUMENTS

| | | |
|---|---|---|
| DE | 9016235 U1 | 4/1991 |
| DE | 4234957 | 10/1992 |
| DE | 10102814 | 1/2002 |
| EP | 364783 | 10/1988 |
| EP | 722891 | 1/1995 |
| EP | 937475 | 2/1998 |
| EP | 1177802 A1 | 2/2002 |
| EP | 1525873 | 4/2005 |
| FR | 1144814 | 3/1956 |
| FR | 2186402 | 1/1974 |
| FR | 2 593 144 | 7/1987 |
| FR | 2752410 | 8/1996 |
| GB | 926159 | 8/1960 |
| GB | 1579065 | 3/1976 |
| GB | 1579065 | 9/1977 |
| GB | 2179526 | 2/1986 |
| GB | 2188305 | 3/1986 |
| JP | 3-267063 A | 11/1991 |
| WO | 82/03556 | 10/1982 |
| WO | 02/34198 | 10/2000 |
| WO | 03/084597 | 10/2003 |

OTHER PUBLICATIONS

Final Office Action mailed Nov. 19, 2008, in U.S. Appl. No. 11/407,608, which was filed Apr. 20, 2006 by Sparholt et al.
Response and Amendment (including most recent claims) to the Final Office Action dated, submitted Feb. 19, 2009, in U.S. Appl. No. 11/407,608 by Sparholt et al.
Office Action mailed Apr. 20, 2009, in U.S. Appl. No. 11/407,608, which was filed Apr. 20, 2006 by Sparholt et al.
Response and Amendment (including most recent claims) to the Non-Final Office Action dated Apr. 20, 2009, and submitted Aug. 18, 2009, in U.S. Appl. No. 11/407,608 by Sparholt et al.
Final Office Action mailed Nov. 3, 2009, in U.S. Appl. No. 11/407,608, which was filed Apr. 20, 2006 by Sparholt et al.
Final Office Action Mailed Sep. 21, 2010 in U.S. Appl. No. 11/628,293, filed Jan. 2, 2008 by Fristrup et al.
Non-Final Office Action Mailed Mar. 24, 2011 in U.S. Appl. No. 11/628,293, filed Jan. 2, 2008 by Fristrup et al.
Examiner'S Answer to Appeal Brief Mailed Sep. 16, 2010 for U.S. Appl. No. 11/407,608, filed Apr. 20, 2006 by Sparholt et al.
English language abstract of DE 4 234 957 (unverified), Apr. 21, 1994.
English language abstract of EP 0 364 783 (unverified), Apr. 25, 1990.
English language abstract of FR 2 593 144 (unverified), Jul. 24, 1987.
English language abstract of FR 2 752 410 (unverified), Feb. 20, 1998.
Notice of Allowance mailed Feb. 5, 2008, from U.S. Appl. No. 11/407,608, an application filed Apr. 20, 2006 by Sparholt et al.
Response filed Mar. 3, 2008 (including most recent claims) in U.S. Appl. No. 11/407,608.
DE 2160939 Machine Translation, Jun. 20, 1971.
FR 2186402 Machine Translation, Jan. 11, 1974.
Office Action mailed Jun. 8, 2004 in Danish Application No. PA 2003 01546, filed Oct. 21, 2003 by Sparholt et al.
International Search Report and Written Opinion issued in connection with PCT Application No. PCT/DK2004/000724, mailed Jun. 30, 2005.
Written Opinion mailed May 4, 2006 in PCT Application No. PCT/DK2004/000724.
Office Action mailed Feb. 14, 2007 in European Application No. 04762943.1 filed Oct. 21, 2004 by Sparholt et al.
Non-Final Office Action mailed Jan. 11, 2010 in U.S. Appl. No. 11/628,293, filed Jan. 2, 2008 by Fristrup et al.
Notice of Appeal in Response to Final Office Action of Nov. 3, 2009, submitted Mar. 2, 2010 in U.S. Appl. No. 11/407,608, filed Apr. 20, 2006 by Sparholt et al.
Non-Final Office Action mailed Oct. 5, 2007 in U.S. Appl. No. 11/407,608, filed Apr. 20, 2006 by Sparholt et al.

* cited by examiner

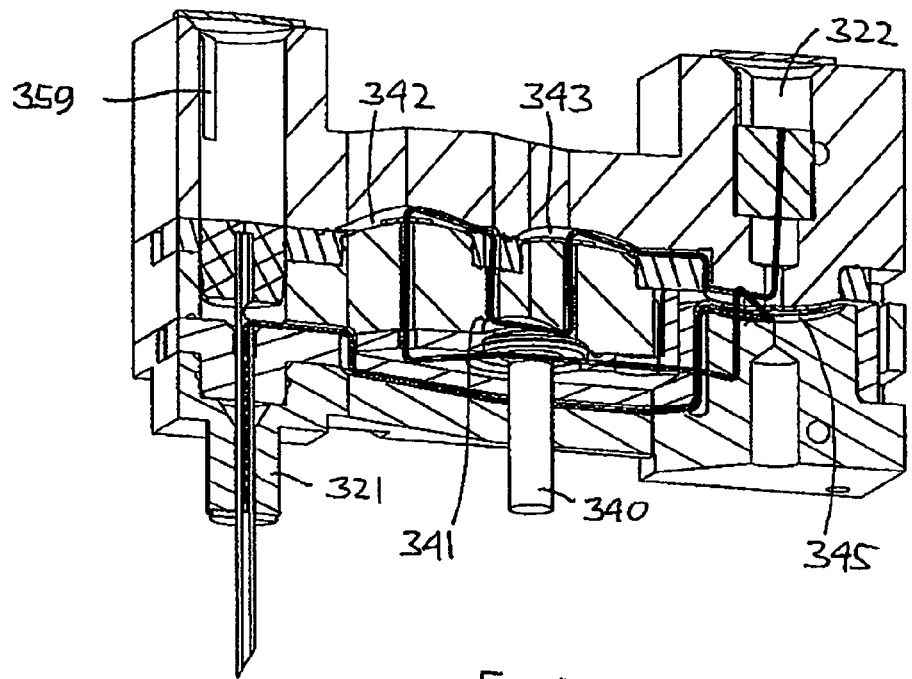
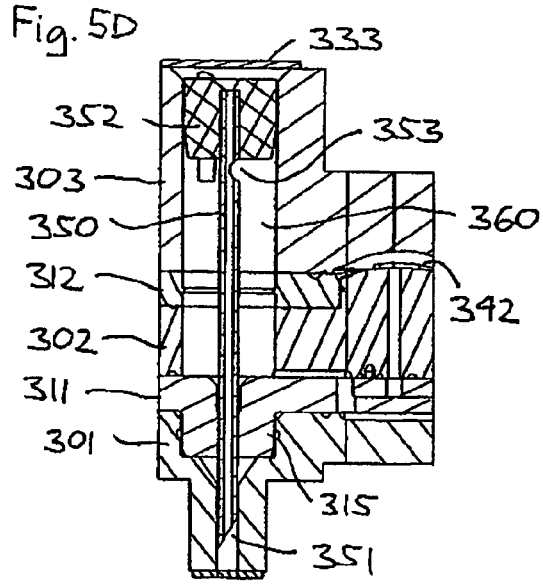
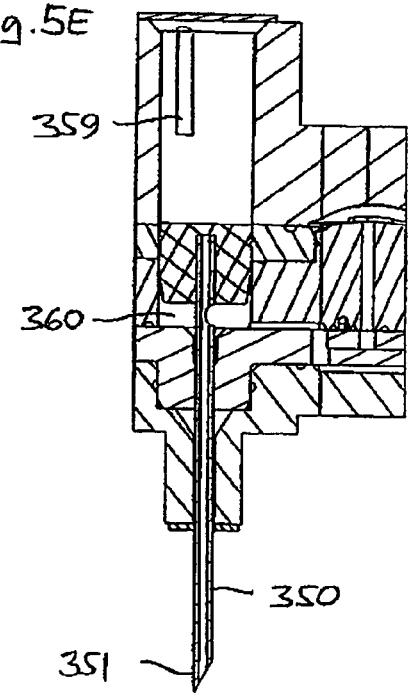

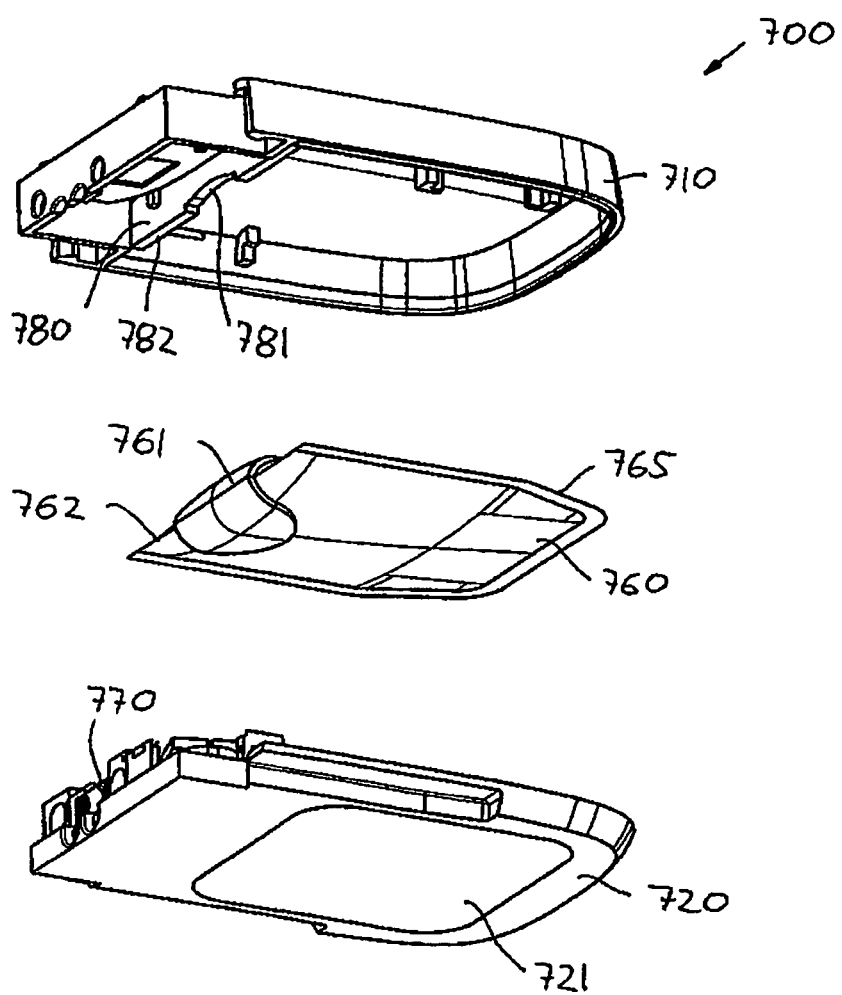

RESERVOIR DEVICE WITH INTEGRATED MOUNTING MEANS

CROSS REFERENCE TO RELATED APPLICATIONS

This Application is a continuation of International Application serial no. PCT/DK2004/000725 filed Oct. 21, 2004 and claims priority from Danish Application serial nos. PA 2003 01545 filed Oct. 21, 2003, PA 2003 01590 filed Oct. 28, 2003; European application serial no. EP 03024276.2 filed Oct. 23, 2003 and to U.S. Provisional Application Ser. Nos. 60/518,881 filed Nov. 10, 2003 and 60/518,832 filed Nov. 10, 2003.

FIELD OF THE INVENTION

The present invention generally relates to an apparatus comprising a reservoir for the storage of fluids. The reservoir may be designed to contain in particular medical liquid products such as drugs, drug solutions, infusion solutions, parenteral solutions, dialysis solutions, perfusion solutions, chemical and alimentary liquids, human blood and its fractions, and the like. The reservoir may also be used for other purposes, e.g. calibration liquids for analytical equipment.

BACKGROUND OF THE INVENTION

In the disclosure of the present invention reference is mostly made to liquids in the form of medical liquids as outlined above, however, this is only an exemplary use of the present invention.

A medical liquid is often supplied in a reservoir (e.g. a container, bag or bottle) which can be accessed by means of a hollow needle, the needle typically penetrating a dedicated connection element (or access means) of the reservoir to provide a fluid communication with the interior of the reservoir. The needle access may be used either for withdrawing liquids from the reservoir or for supplying a liquid to the reservoir. For example, when preparing the fluids which are to be administrated to the body of a patient from a given reservoir, it is common that medically effective substances are supplied to a pre-sealed reservoir which is filled with a transport fluid, usually in the form of sodium chloride solution or a glucose solution, the diluted drug then being given to a patient intravenously via an intravenous (IV) infusion set. For this type of use, the reservoir may be provided with a single connection means adapted to be used for both purposes, or the reservoir may comprise two connection means adapted for their respective purposes, e.g. for a larger infusion set outlet needle and a smaller drug injecting needle. The connection element may be adapted to be opened manually to provide an opening, through which a needle subsequently can be inserted, or the pointed needle can be used for penetrating the connection element, which may be of the self-sealing type, e.g. the connection element will seal the reservoir after the needle has been withdrawn.

In case the reservoir is of glass, the connection element will be a separate element which is mounted to the glass reservoir by special means, however, for plastic reservoirs the connection element will typically be formed integrally with the reservoir. One of the most widely used type of plastic reservoirs for medical use is in the form of a flexible infusion bag comprising at a lower portion thereof one or more needle-penetratable connection elements. Such bags are typically formed from flexible foil sheets which are joined to form an internal space. Depending on the actual construction of the bag, the connection element(s) may be arranged either on a surface portion of a foil sheet or may be arranged corresponding to an edge portion of the reservoir. For the latter type, the connection element is typically positioned and held in place between two foil sheets connected to each other by welding.

For both of the above two arrangements, the self-sealing element is normally carried by a tubular member connected to the bag in either of the above two ways. For example, U.S. Pat. No. 4,362,158 shows an infusion bag in which a tubular nozzle member is connected to an infusion bag corresponding to a free surface thereof, a self-sealing rubber seal member being mounted on the nozzle.

For some liquids, e.g. certain types of drugs, it is desirable if the elastomeric material from which the seal member normally is manufactured, does not come in contact with drug. To solve this problem, European patent application EP 0 364 783 describes a medicament bottle having an external sealing element held in place by a separate cap member attached to the outer surface of the bottle, and FR 2 752 410 discloses a medicament bag in which a needle-penetratable member is attached to an outer surface of the bag.

U.S. Pat. No. 6,074,369 discloses an injection device comprising a flexible reservoir formed from two Belleville spring diaphragms and with a needle-penetratable member arranged between the two diaphragms. The reservoir is mounted in a housing by mounting means engaging the diaphragms.

The above reservoirs are relatively large typically comprising 100-1000 ml of liquid, however, reservoirs which can be accessed by a penetrating needle member is also used for much smaller volumes. For example, certain calibration solutions for calibrating analytical equipment are supplied in small bag-like reservoirs containing a few ml. When properly designed, such small reservoirs may also be used for drug purposes.

DISCLOSURE OF THE INVENTION

Having regard to the above-described reservoirs and devices, it is an object of the present invention to provide an apparatus comprising a liquid reservoir which can be manufactured and used in an efficient manner. It is a further object of the invention to provide an apparatus which is convenient and safe in use and allows a varity of applications. It is a yet further object of the invention to provide a reservoir which can be used with a varity of liquids. Further objects and advantages will become apparent from the disclosure of the invention and the description of the exemplary embodiments.

In the disclosure of the present invention, embodiments and aspects will be described which will address one or more of the above objects or which will address objects apparent from the below disclosure as well as from the description of exemplary embodiments.

More specifically, in a first aspect of the invention an apparatus is provided comprising a housing comprising mounting means (e.g. arranged within or formed by the housing), a flexible reservoir adapted to contain a fluid and comprising a septum member formed from a needle-penetratable flexible material (e.g. an elastomeric material), at least a portion of the flexible reservoir being arranged within the housing, wherein the mounting means engages the septum member to thereby mount the flexible reservoir relative to the mounting means. In this way a secure fixation between the reservoir and the mounting means is provided without having to interfere with the general flexibility of the reservoir, e.g. substantially the entire flexible reservoir apart from the outlet/mounting means may be arranged free to move relative to the mounting means, this allowing the reservoir to be emptied to a high degree.

Typically, the housing will be closed with the reservoir arranged there within, however, in principle it may be open in which case the housing would serve as a supporting structure which in the context of the present invention is included in the term housing. The mounting means may be fixed relative to the housing or may be moveable relative to the housing, e.g. the mounting means may be slideable relative to the housing this allowing the reservoir to be moved into engagement with other structures such as a pump assembly.

In an exemplary embodiment the septum is self-sealing. Although the term "self-sealing" will be clear to the skilled person, it should be noted that this is not to be regarded as an absolute term for a given septum but that it will depend upon the intended use for a given reservoir. For example, a given septum will be designed to be self-sealing in connection with needles of a given range of gauges (i.e. diameters) and with a given design for the pointed distal end. Thus, a relatively thin septum adapted to be used with a correspondingly thin needle may not be self-sealing when penetrated by a larger needle. Further, if the reservoir is pressurized above the intended internal pressure, a punctuated septum may leak.

By the term "adapted to contain" is defined that a reservoir in accordance with the invention may be provided in an empty state for subsequent filling, or that it may be filled during manufacture of the reservoir to provide a prefilled reservoir.

The reservoir may comprise first and second flexible foil portions sealed together (e.g. provided by to separate foil members or a single folded foil member) to form an enclosed cavity for containing the fluid, the reservoir having a pouch-like configuration.

If the fluid (liquid or gas) to be contained in the reservoir does not require specific properties for the surrounding walls (e.g. in respect of evaporation, leakage or chemical inertness), the first wall portion may be made from a single layer of material or the reservoir in general may be formed from a single material. If the fluid requires specific properties for the reservoir, the reservoir may be provided with an outer surface generally formed from a first material and an inner surface generally formed from a second material. The wall portion providing the first mounting surface may be of a special construction (e.g. allowing needle-penetration) with the rest of the reservoir wall having different properties.

The reservoir may comprise at least first and second flexible foil (or film) members sealed together to form at least one enclosed cavity for containing the liquid. The foil members may be provided as two or more separate members or as a single member which is folded upon itself. The foil members may be composite laminates of continuous layers including an outer layer and an inner layer. This would allow the outer surface to be optimized for connection of the septum whereas the inner surface may be optimized in respect of reservoir properties in respect of the fluid to be contained. Any laminate referred to in the present application may be a traditional laminate, a co-extrudate or an extrusion-laminate. The walls defining the reservoir may be formed from a single material or single type of laminate, or different materials or laminates may be used for different wall portions of the reservoir.

The foil members may comprise an intermediate layer, the inner layer being formed from a weldable material, which would allow the foil members to be sealed together at least partially by welding corresponding to the peripheries of the bag. In case the outer layer solely provides the mounting surface for the septum, the "intermediate" layer may provide the outer layer for a portion of the reservoir. To allow a contained liquid to be viewed through the reservoir wall, at least a portion thereof may be formed by a transparent or translucent material.

Just as a portion of the outer reservoir wall surface may be optimized for attachment of the septum by welding, also the septum mounting surface may be optimized. For example, the septum may be a laminate comprising two or more layers, the "lower" layer providing the mounting surface. The septum may be welded to the reservoir corresponding to substantially the entire mounting surface, however, it may also be welded using one or more (concentric) circumferential welds.

The septum may be configured to provide additional properties in addition to the sealing properties. For example, a portion of the septum or the entire septum may be configured to flex together with the portion of the reservoir to which it is mounted, this allowing the septum to be bend either during manufacture or during use. To allow this flexibility the septum may be in the form of a relatively thin member or may comprise a relatively thin portion. Further, when the septum is arranged "naked" on the reservoir, it may be accessed from a wide range of angles.

In an exemplary embodiment the apparatus further comprises a fluid conduit having an inlet and an outlet, the inlet being adapted to be arranged in fluid communication with the reservoir outlet means, wherein the fluid conduit and the reservoir are moveable relative to each from an initial position in which there is no fluid communication therebetween and a connected position in which the inlet of the fluid conduit is arranged in fluid communication with the reservoir through the reservoir outlet means. The fluid conduit may be in the form of (or comprise) a pointed needle.

In an exemplary embodiment, the apparatus further comprises an expelling assembly adapted to expel a fluid (e.g. a drug) contained in the reservoir through the outlet of the reservoir. The expelling assembly may be adapted to force or suck the drug from the reservoir. In the latter case the expelling assembly may be in the form of a suction pump having an inlet and an outlet and an internal flow path arranged therebetween, the inlet being adapted to be arranged in fluid communication with the reservoir through the needle.

The reservoir and the expelling assembly may be arranged moveable relative to each other. In case the reservoir is moveable this implies that the mounting means is also moveable relative to the expelling assembly and the housing. Alternatively, the reservoir and the expelling assembly may both be fixed relative to each other, the fluid communication being provided by a moveable fluid connector which advantageously is formed as part of the expelling assembly and serving as an inlet therefore. More specifically, a fluid connector may be arranged within the interior of the expelling assembly in an initial state, the fluid connector comprising an inlet and an outlet, wherein the fluid connector is arranged to be operated from the initial state and to an operating state in which fluid communication is established between the interior of the reservoir and the interior of the expelling assembly via the fluid connector and with the outlet of the fluid connector being arranged in the flow path of the expelling assembly.

The apparatus may be in the form of skin-mountable pump device further comprising a transcutaneous device adapted to penetrate the skin of a subject, a mounting surface adapted for application to the skin of the subject, wherein the reservoir comprises a fluid drug, and the expelling assembly, in a situation of use, is adapted for expelling the drug out of the reservoir and through the skin of the subject via the transcutaneous device. The transcutaneous device may be in the form of a pointed hollow infusion needle, a micro needle array, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle. The reservoir may be supplied pre-filled to the user or adapted to be filled (and refilled) by the user.

The present invention also provides a method of mounting a flexible reservoir, comprising the steps providing a supporting structure comprising mounting means, providing a flexible reservoir comprising a needle-penetratable self-sealing septum member, and engaging the septum member and the mounting means, the mounting means thereby gripping or engaging the septum member to properly fix and position it relative to the mounting means.

When the reservoir comprises first and second flexible foil portions sealed together to form a reservoir having a pouch-like configuration, this may be accomplished by a reservoir having welded areas arranged along a peripheral portion of the reservoir as well as folded over portions. Mounting means may engage the welded and/or folded over peripheral portions to properly hold the reservoir in place, either in addition to the mounting means engaging the septum member or alone. For example, if the reservoir is sufficiently rigid the mounting means engaging the reservoir at a peripheral portion thereof may properly position the septum member without engaging the septum.

As discussed above, a "naked" septum arrangement may be adapted to allow insertion of a needle at an angle which may differ from perpendicular. Correspondingly, in a further aspect of the invention an apparatus is provided comprising a flexible reservoir comprising first and second flexible foil portions sealed together to form an enclosed cavity for containing a fluid, the reservoir having a pouch-like configuration defining a general plane, a needle-penetratable outlet being arranged on a portion of the reservoir which is inclined relative to the general plane. Indeed, the outlet will have to be adapted to provide a seal around the needle to avoid any substantial leakage. The apparatus further comprises a needle having a generally straight inlet portion and an outlet, the inlet being adapted to be arranged in fluid communication with the reservoir, wherein the needle and the reservoir are arranged moveable relative to each from an initial position in which there is no fluid communication therebetween and a connected position in which the needle inlet is arranged in fluid communication with the reservoir through the reservoir outlet, and wherein the needle in the connected position penetrates the reservoir outlet substantially in parallel with the general plane.

The reservoir may be made from e.g. two separate foil members welded together at the periphery thereof (e.g. at four sides for a square reservoir), by a folded-over foil welded together at the remaining peripheral portion (e.g. at three sides for a square reservoir), or from a foil tube welded together at the two ends thereof. Thus, for a typical bag- or pouch-formed reservoir the welds (e.g. two opposed welds) can be used to define the general plane of the reservoir, although it would be possible to arrange the welds at other locations. When the reservoir is filled it will typically bulge out to provide one or more convex surfaces, which apart from the "top" area will be arranged inclined relative to the general plane. To present a portion of the foil surface which is more inclined than that of the reservoir in its "inherent" configuration, a portion of the reservoir may be deflected relative to the remaining portion of the reservoir, e.g. bend along a line, this aiding the insertion of the needle into the reservoir.

The outlet may be provided by any suitable structure allowing a needle to be brought in fluid communication with the interior of the reservoir without. If the foil material from which the reservoir is formed would allow a needle to puncture the foil in a non-leaking manner no additional member would have to be provided, however, in most circumstances an additional outlet member will have to be provided.

For example, the reservoir outlet means may be in the form of a septum member formed from a needle-penetratable self-sealing material as described above, the septum advantageously being connected by welding. The septum may cover portions of the reservoir in addition to those forming the outlet, e.g. the septum may be arranged on a rounded edge portion of the reservoir thereby also covering a portion of the reservoir which is oriented perpendicularly relative to the general plane. Dependent upon the fluid to be contained in the reservoir, the walls thereof may comprise one or more layers as described above.

In preferred embodiments the inclined angle is less than 45 degrees, preferably less than 30 degrees and more preferably less than 15 degrees (with parallel being defined as zero degrees). By introducing the needle at an inclined angle, the reservoir may collapse fully or partially without the needle penetrating the reservoir portion arranged opposite the outlet means.

In exemplary embodiments the above-described inclined needle arrangement may be used in combination with an expelling assembly and a transcutaneous device to provide a delivery device as described above.

As described above, a reservoir comprising a septum is provided in combination with additional structures for mounting and/or connecting the reservoir. Thus, corresponding to a further aspect of the invention, a reservoir per se is provided adapted to contain a fluid within a cavity formed by walls, comprising a first wall portion formed from a needle-penetratable material, where the wall portion comprises an outer first mounting surface. The reservoir further comprises a septum member (in the following also referred to as septum) formed from comprises a septum member (in the following also referred to as septum) formed from a needle-penetratable self-sealing material, the septum member comprising a second mounting surface, wherein the septum member, corresponding to the second mounting surface, has been mounted on the first mounting surface by means of welding together the two surfaces. The material for the first mounting surface may be located solely corresponding to the placement of the septum, or it may cover a portion or the entire exterior surface of the reservoir. The reservoir may be a relative rigid reservoir (e.g. a blown bottle) or a more flexible reservoir as a traditional IV bag or a reservoir as described above.

Although the septum may be mounted alone, it may be desirable to provide additional mounting means allowing access means such a tubing to be connected to the reservoir, e.g. as described above with respect to the known IV bags. For example, a tubular connector protruding from the surface of the reservoir may be attached around the septum, e.g. circumferentially. In this way the two components can be attached independently of each other without having the septum to be mounted to the connector, although it may be convenient to attach the two components to the reservoir simultaneously during a welding procedure.

The septum may also be configured to serve additional purposes. For example, in case the reservoir is in the form of a flexible reservoir adapted to be mounted in a drug delivery device as described above, the septum may be used to handle the reservoir during the mounting procedures just as the septum may be adapted to serve as a connecting means between the reservoir and the delivery device, e.g. the septum member may be welded to the delivery device or the septum member and the delivery device may be provided with mating coupling means.

The septum and the materials forming the reservoirs in accordance with the different aspects of the present invention may be selected in accordance with the above described embodiments and their intended use. For example, the wall portion providing the first mounting surface may be manufactured from or comprise polyethylene (PE), polypropylene (PP), oriented polypropylene (OPP), amorphous polyester (PET), oriented amorphous polyester (OPET), polyamide (PA) or oriented polyamide (OPA). The septum portion forming the second mounting surface may be manufactured from a thermoplastic elastomeric (TPE) material, e.g. an oleophenic based thermoplastic material or an oleophenic based thermoplastic vulcanisate, or blends thereof. More specifically, the TPE may be a thermoplastic vulcanisate composed of bromo-butyle rubber in a polypropylene matrix (e.g. as sold under the trade name Trefsin), a thermoplastic vulcanisate composed of EPDM rubber in a polypropylene matrix (e.g. as sold under the trade name Santoprene), or a styrene ethylene butylene styrene (SEBS) copolymer based elastomere (e.g. as sold under the trade name Kraiburg). Also TPU, TPE-A or TPE-E may be used.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

Herein the term "insulin" refers to insulin from any species such as porcine insulin, bovine insulin, and human insulin and salts thereof such as zinc salts, and protamin salts as well as active derivatives of insulin, and insulin analogues. The term "active derivatives of insulin", is what a skilled art worker generally considers derivatives, vide general textbooks, for example, insulin having a substituent not present in the parent insulin molecule. The term "insulin analogues" refers to insulin wherein one or more of the amino acid residues have been exchanged with another amino acid residue and/or from which one or more amino acid residue has been deleted and/or from which one or more amino acid residue has been added with the proviso that said insulin analogue has a sufficient insulin activity.

The material(s) used to form the reservoir or reservoir devices of the present invention may be selected in accordance with the intended use. Thus it may be required that the material(s) fulfil(s) specified functional requirements such as physical properties for the material after sterilization, chemical requirements for the material after sterilization, and cleanliness. Correspondingly, the material may be sterilizeable using e.g. gamma irradiation, electron beam, steam, or ethylene oxide. The material(s) may further be selected in accordance with one or more of the following requirements: 1) the material must be transparent, 2) the material must provide a good barrier against water evaporation; 3) the material must provide a good barrier against gasses (for example, oxygen and carbon dioxide); 4) the material must provide a good barrier against preservatives (for example, phenol and metacresol); 5) the material must provide a good barrier against odors (for example preservatives); 6) the material must be resistant against environmental stress cracking (for example, oils, perfumes); 7) the material must be resistant against flexcrack; 8) the material must have good sealing properties (for example, by welding); 9) the material must not delaminate after sterilization, during processing or storage; 10) the material must not relax significantly during storage and use, 11) the material must not emit substances to the drug which can affect the health and safety of the patient (leachables); 12) the material must have a very low level of extractables; and 13) the material must be compatible with a contained drug formulation. It may further be relevant that the material(s) fulfil(s) certain health and safety requirements, preferably most of or all the requirements mentioned in 1) European Pharmacopoeia (Ph. Eur.) 2002, $4^{th}$ edition; 2) The United States Pharmacopeia (USP) 25; 3) Japanese Pharmacopeia (JP) XIV; 4) EEC Directive 90/128+amendments "Relating to plastics materials and articles intended to come into contact with foodstuffs"; 5) Code of federal regulations (CFR) Title 21 Food and Drugs, part 170-190; 6) III/9090/90 EN. Plastic Primary Packaging Materials. Note for Guidance; and 7) Guidance for Industry. Container Closure Systems for Packaging Human Drugs and Biologics, Chemistry, Manufacturing, and Controls Documentation. FDA, May 1999.

In respect of laminates the following definitions are used: Co-extrusion covers a process where two or more polymer materials are melded in two or more extruders and co-extruded together through a flat nozzle or systems of flat nozzles and cooled to form the co-extruded foil. Extrusion-lamination covers a process where a feedstock in form of a foil of one material is coated through a flat nozzle or systems of flat nozzles from one or more extruders with one layer or more layers of melted material or materials and then cooled to form the extrusion-lamination foil. "Traditional" lamination covers a process, where two feed stocks of foil materials are joined together by adding a proper adhesive to one foil, followed by addition of the second foil forming the laminated foil. A tie layer is a layer which is placed between two polymer layers with the object of securing that the two layers are joined together.

BRIEF DESCRIPTION OF THE DRAWINGS

In the following exemplary embodiments will be further described with references to the drawings, wherein FIG. 5C shows a cross-sectional view of the pump assembly of FIG. 5C, FIGS. 5D and 5E show partial cross-sectional views of the pump assembly of FIG. 5C, FIG. 8 shows an exploded view of a further reservoir unit.

In the figures like structures are mainly identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as the relative dimensions are intended to serve illustrative purposes only.

Figure 1:
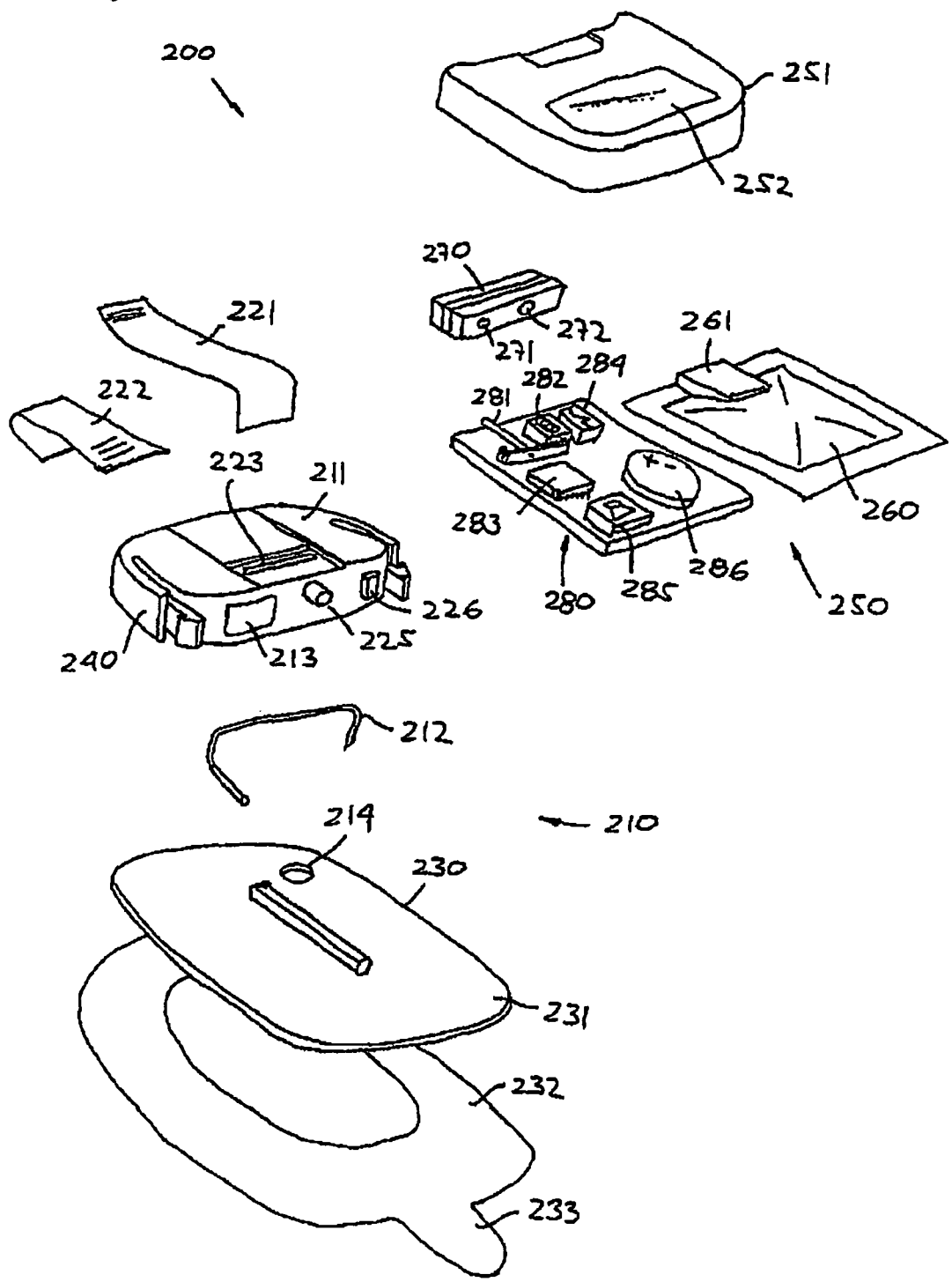
FIG. 1 shows a perspective view of a drug delivery device.

In FIG. 1 an embodiment of a drug delivery device is shown, the device comprising a flexible reservoir allowing one or more aspects of the present invention to be implemented.

More specifically, FIG. 1 shows in an exploded perspective view a medical device in the form of a drug delivery device 200 comprising a needle unit 210 having a needle housing 211, a base member 230 with a lower mounting surface adapted for application to the skin of a subject, and a separate reservoir and pump unit 250. In the shown embodiment the base member comprises a relatively rigid upper portion 231 attached to a more flexible adhesive patch member 232 provided with a gripable strip and having a lower adhesive surface providing the mounting surface per se. In the shown embodiment the needle housing is attached to the base plate as a separate unit, the two elements in combination forming the needle unit. Within the housing a hollow infusion needle 212 is pivotally arranged.

The needle unit comprises first and second openings 213, 214 which may be open or covered by needle penetratable membranes to provide a sealed interior. The needle comprises a proximal inlet end and a pointed distal outlet end. The housing further comprises actuation means (not shown) for moving the needle between a retracted and extended state, and retraction means (not shown) for moving the needle between the extended and a retracted position. The actuation and retraction means are actuated by gripable first and second strip members 221, 222 connected to the respective means through slot-formed openings in the housing, of which the slot 223 for the first strip can be seen. The second strip is further connected to the patch strip 233. Arranged on the housing is user-actuatable male coupling means 240 in the form of a pair of resiliently arranged hook members adapted to cooperate with corresponding female coupling means on the reservoir unit. The housing further comprises connecting means 225 for establishing fluid communication between the pump unit and the reservoir (see below), and communication means 226 for activating and deactivating the expelling means.

The reservoir unit 250 comprises a housing 251 in which a reservoir and expelling means are arranged, the expelling means comprising a pump unit 270 and control and actuation means 280 therefore. The reservoir 260 is in the form of prefilled, flexible and collapsible pouch comprising a needle-penetratable septum 261 welded thereto and adapted to be arranged in fluid communication with the pump unit via a pump inlet 272. The reservoir is in the form of a flat pouch arranged substantially in parallel with the general plane of the device, the septum being mounted on an initially convex upper surface of the reservoir, thereby allowing a needle to be introduced therethrough substantially in parallel with the upper and lower walls of the reservoir. The housing comprises mounting means (not shown) allowing the septum to be fixated relative thereto, and a window 252 allowing the user to inspect the content of the reservoir. The shown pump is a mechanically actuated membrane pump, however, the expelling means may be of any suitable configuration.

The control and actuation means, which may be arranged on a PCB or flex-print, comprises a pump actuating member 281 in the form of a lever and piston arrangement driven by a coil actuator 282, a microprocessor 283 for controlling, among other, the pump actuation, a contact switch 284 cooperating with the communication means 226 on the needle unit, signal generating means 285 for generating an audible and/or tactile signal, and an energy source 286.

Figure 2:
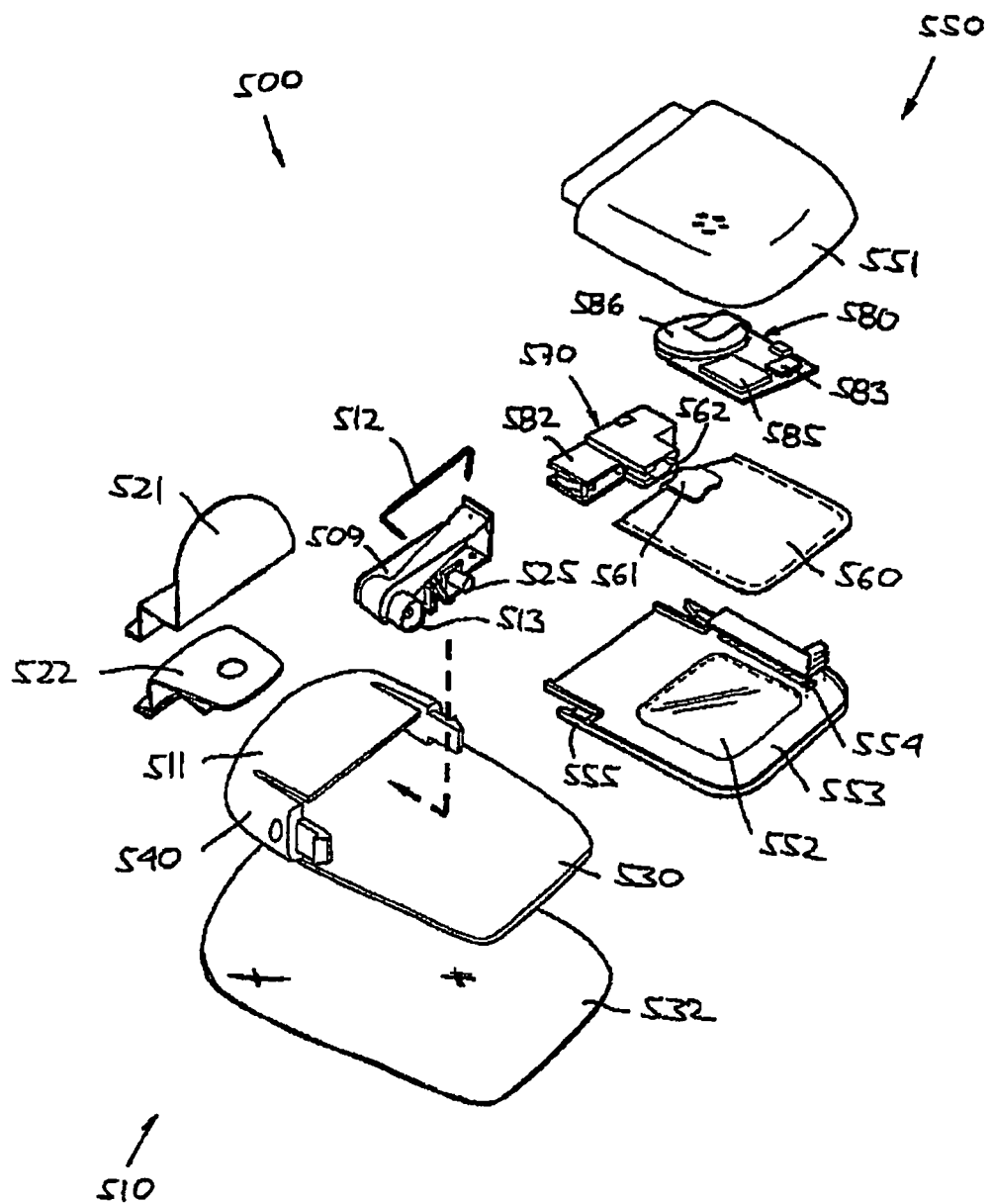
FIG. 2 shows a perspective view of a further drug delivery device.

In FIG. 2 a drug delivery device having the same general configuration as in FIG. 1 is shown. More specifically, FIG. 2 shows a drug delivery device 500 comprising a needle unit 510 having a housing portion 511 and a relatively rigid base portion 530 attached to a more flexible adhesive patch member 532 having a lower adhesive surface providing the mounting surface per se. Within the housing a needle actuation unit 509 is arranged, the needle actuation unit comprising a hollow infusion needle 512 pivotally arranged relatively to the base plate.

The inlet portion of the needle is arranged corresponding to the pivoting axis, the inlet portion being protected by a cylindrical member 513 protecting the user against accidental needle pricks. Adapted to cooperate with the actuation and retraction strips 521, 522 the needle actuation unit 509 comprises actuation means for moving the needle between a retracted and extended state, and retraction means for moving the needle between the extended and a retracted position. The needle unit further comprises male 540 and female (not shown) coupling means adapted to cooperate with corresponding female and male 555 coupling means on the reservoir unit, as well as connecting means 525 for establishing fluid communication between the pump unit and the reservoir (see below).

The reservoir unit 550 comprises a housing, formed from upper and lower housing portions 551, 553, in which a reservoir and expelling means are arranged, the expelling means comprising a pump unit 570 and control means 580 therefore. The lower housing portion comprises two windows 552, 554 allowing the user to inspect the content of the reservoir respectively a reservoir indicator (see below). The reservoir 560 is in the form of prefilled, flexible and collapsible pouch formed from a flexible foil folded corresponding to one edge of the reservoir and sealed along the remaining three edges, the reservoir comprising a needle-penetratable septum 561 welded thereto corresponding to the rounded, folded edge. The pump unit which in the shown embodiment is in the form of a membrane pump comprises a pump actuating member in the form of a coil actuator 582 operatively connected to thereto, and a mounting means in the form of a slot 562 allowing the septum to be mounted and fixed relative to the inlet means of the pump.

The control means comprises a microprocessor 583 for controlling, among other, the pump actuation, a signal generating means 585 for generating an audible and/or tactile signal, and an energy source 586. A reservoir indicator 582 for indicating to the user an amount of drug left in the reservoir is coupled to the control means. The indicator may be in the form of an electrochemical strip of the type used in e.g. batteries.

Figure 3:
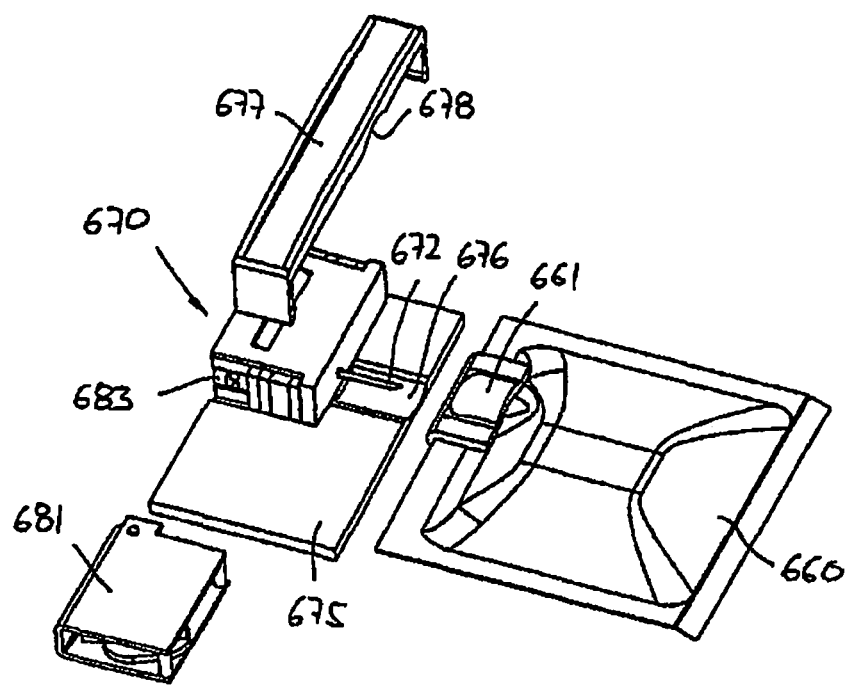
FIGS. 3 and 4 show a pump unit and reservoir connection.
Figure 4:
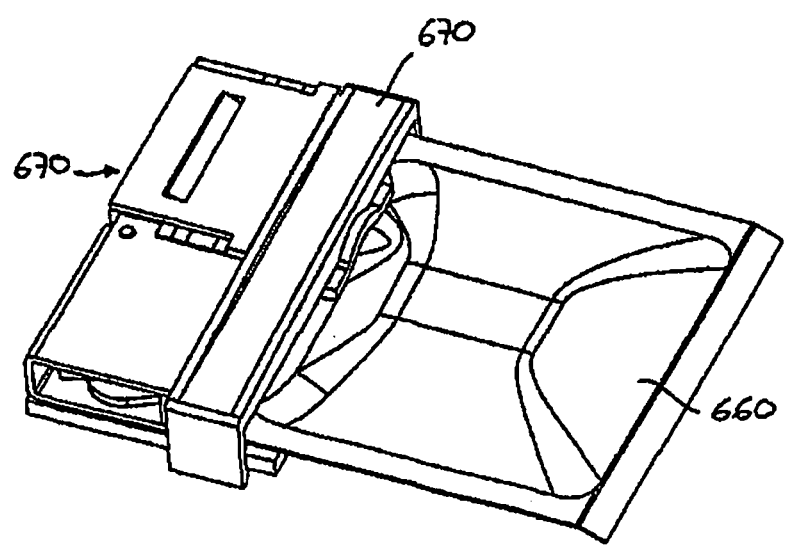

With reference to FIGS. 3 and 4 an alternative configuration for the reservoir mounting means is shown. The pump unit 670 comprises a base plate 675 with a first groove portion 676 and a clamp member 677 with a second groove portion 678, the two groove portions being adapted to engage opposed surfaces of the septum member 661 of a reservoir 660 when the clamp member is locked to the base plate as shown in FIG. 4, thereby placing a securing the septum member relative to the pump inlet means 672. The groove portions may be provided with additional gripping means (e.g. protrusions, not shown) preventing the septum from sliding out of engagement with the mounting means. In the shown embodiment the pump inlet means is in the form of a pointed hollow needle projecting from the pump unit prior to mounting of the reservoir, however, advantageously fluid communication between the pump unit and the reservoir may not be established when the reservoir is mounted but just prior to use, this as explained in greater detail below. In the shown embodiment the septum is clamped between a portion of the pump and a separate clamp member, however, one or both of these structures may be formed integrally with housing portions, e.g. an upper and a lower housing portion.

The pump unit further comprises a coil actuator 682 adapted to engage a piston member 683, 340 of a membrane pump (see below). In the shown embodiment the base plate 675 and the clamp member 677 are separate structures, however, these may be formed integrally with e.g. upper respectively lower housing portions.

In FIG. 8 an exploded view of a further reservoir unit is shown, the unit comprising an upper housing member 710, a lower housing member 720 with a transparent area 721, a flexible reservoir 760 with a rounded edge portion 762 on which a septum member 761 is mounted, a pump assembly 770 with actuator and a circuit board (not shown) arranged above the reservoir and comprising electronic components for controlling actuation of the pump. The upper and lower housing members comprise mounting means in the form of opposed upper and lower ridge portions 780 (the lower not seen) adapted to engage and mount the reservoir in the housing. Each ridge portion comprises a central cut-out portion 781 adapted to engage the septum member on its opposed surfaces when the housing members are assemble thereby locking the reservoir in place within the housing. The degree of locking will be determined by the pressure exerted on the septum member, the elastic properties of the septum member and the friction between the ridge and the septum member. On each side of the cutout portion the ridge portions comprise a straight portion 782 which may aid in mounting the reservoir in the housing. The straight portions may engage the initially prefilled reservoir to help lock it in place, however, as the reservoir is emptied and flattens this grip may lessen. In contrast, the engagement with the septum is adapted to properly hold the reservoir in place as the reservoir is emptied. The straight portions may also be adapted to pinch and fully flatten the reservoir thus serving as an additional mounting means. Additional mounting means (not shown) may engage and grip the reservoir at other locations, e.g. along the welded edges 765.

Figure 5A:
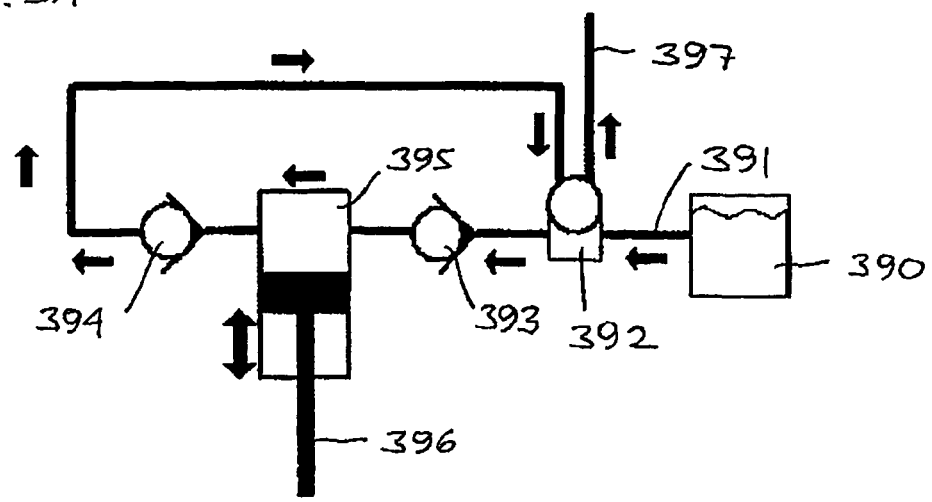
FIG. 5A shows a schematic overview of a pump connected to a reservoir.

With reference to FIG. 5A a schematic overview of a pump connected to a reservoir is shown, the pump comprising the following general features: a fluid connection 391 to reservoir a reservoir 390, a safety valve 392, inlet and outlet valves 393, 394, a pump chamber 395 with an associated piston 396, and an outlet 397. The arrows indicate the flow direction between the individual components. When the piston is moved downwards (in the drawing) a relative negative pressure will build up inside the pump chamber which will cause the inlet valve to open and subsequently fluid will be drawn form the reservoir through the open primary side of the safety valve. When the piston is moved upwards (in the drawing) a relative over-pressure will build up in the pump chamber which will cause the inlet valve to close and the outlet valve and the safety valve to open whereby fluid will flow from the pump chamber through the outlet valve and the secondary side of the safety valve to the outlet. As appears, in normal operation the safety valve allows fluid passage during both intake and expelling of fluid and is thus "passive" during normal operation. However, in case the reservoir is pressurized (as may happen for a flexible reservoir) the elevated pressure in the reservoir will be transmitted to both the primary side of the safety valve and, via the pump chamber, the secondary side of the safety valve in which case the pressure on the primary side of the safety valve will prevent the secondary side to open.

Figure 5B:
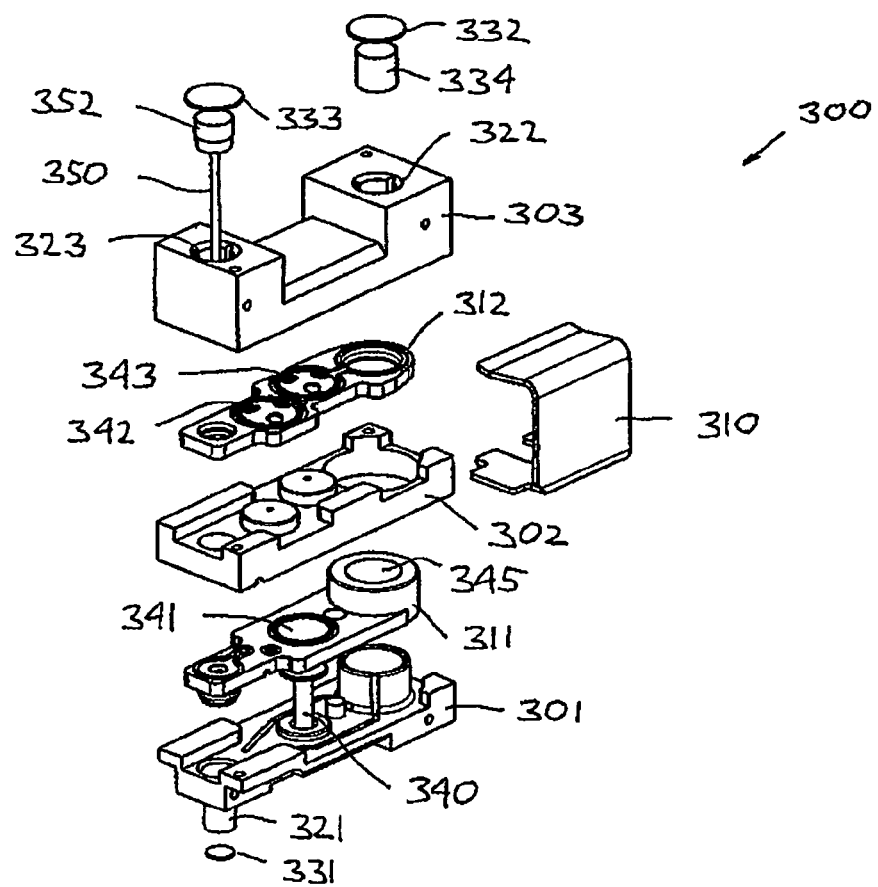
FIG. 5B shows an exploded view of a pump assembly.
Figure 6A:
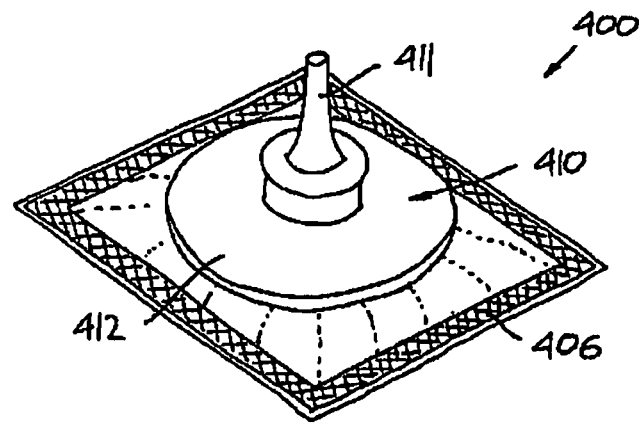
FIG. 6A shows a perspective view of a flexible reservoir.
Figure 6B:
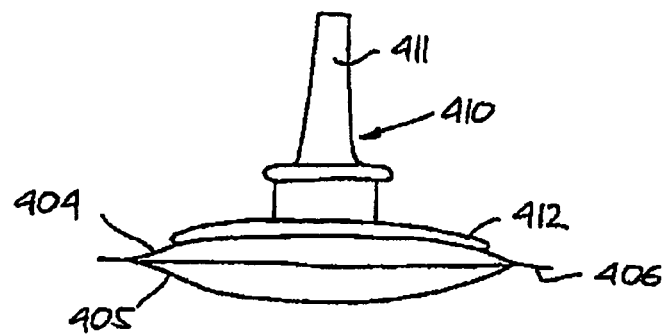
FIG. 6B shows a side view of the reservoir shown in FIG. 6A.
Figure 6C:
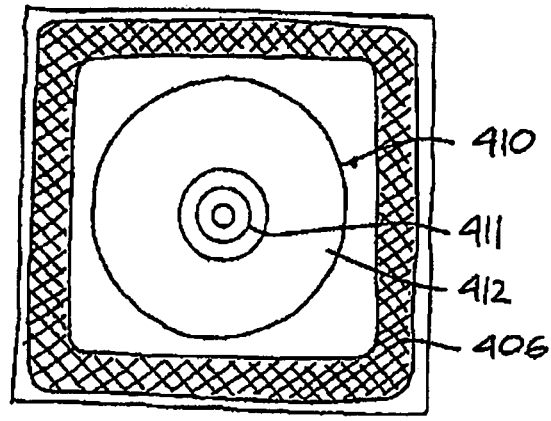
FIG. 6C shows an upper view of the reservoir shown in FIG. 6A.

In FIG. 5B an exploded view of a pump assembly 300 utilizing the pump principle depicted in FIG. 5A is shown, the pump assembly (in the following also referred to as a pump) being suitable for use with the reservoir units of FIGS. 1-4. The pump is a membrane pump comprising a piston-actuated pump membrane with flow-controlled inlet- and outlet-valves. The pump has a general layered construction comprising first, second and third members 301, 302, 303 between which are interposed first and second membrane layers 311, 312, whereby a pump chamber 341 is formed by the first and second members in combination with the first membrane layer, a safety valve 345 is formed by the first and third members in combination with the first membrane layer, and inlet and outlet valves 342, 343 are formed by the second and third members in combination with the second membrane layer (see FIG. 5C). The layers are held in a stacked arrangement by an outer clamp 310. The pump further comprises an inlet 321 and an outlet 322 as well as a connection opening 323 which are all three covered by respective membranes 331, 332, 333 sealing the interior of the pump in an initial sterile state. The membranes are penetratable or breakable (e.g. made from paper) by a needle or other member introduced through a given seal. The outlet further comprises a self-sealing, needle-penetratable septa 334 (e.g. of a rubber-like material) allowing the pump to be connected to an outlet needle. As shown in FIG. 5C a fluid path (indicated by the dark line) is formed between the inlet 321 (see below) and the inlet valve 342 via the primary side of the safety valve 345, between the inlet valve, pump chamber 345 and the outlet valve 343, and between the outlet valve and the outlet 322 via the secondary side of the safety valve, the fluid paths being formed in or between the different layers. The pump also comprises a piston 340 for actuating the pump membrane, the piston being driven by external driving means (not shown).

The pump further comprises a fluid connector in the form of hollow connection needle 350 slidably positioned in a needle chamber 360 arranged behind the connection opening, see FIG. 5D. The needle chamber is formed through the layers of the pump and comprises an internal sealing septum 315 through which the needle is slidably arranged, the septum being formed by the first membrane layer. The needle comprises a pointed distal end 351, a proximal end on which is arranged a needle piston 352 and a proximal side opening 353 in flow communication with the distal end, the needle and the piston being slidably arranged relative to the internal septum and the chamber. As can be appreciated form FIG. 5D the needle piston in its initial position is bypassed by one or more radially placed keyways 359. These are provided in order to allow steam sterilisation and to vent the air otherwise trapped when the fluid connector is moved forward in the needle chamber.

The above-described pump assembly may be provided in a drug delivery device of the type shown in FIG. 2. In a situation of use where the reservoir unit is attached to a needle unit a proximal end of the infusion needle is introduced through the outlet seal and septum 334 of the pump, and the connection member 525 (see FIG. 2) is introduced through the connection membrane 333. By this action the connection needle is pushed from its initial position as shown in FIG. 5D to a actuated position as shown in FIG. 5E in which the distal end is moved through the inlet membrane 331 and further through the needle-penetratable septum of a nearby located reservoir, this establishing a flow path between the reservoir and the inlet valve via the proximal opening 353 in the needle. In this position a seal is formed between the needle piston and the needle chamber.

As appears, when the two units are disconnected, the infusion needle 212 is withdrawn from the pump outlet whereas the connection needle permanently provides fluid communication between the pump and the reservoir.

With reference to FIGS. 6A-6C and 7A-7C an alternative configuration of a flexible, prefilled drug reservoir suitable for use in a delivery device of the type shown in FIGS. 1 and 2 will be described.

The flexible reservoir 400 comprises first and second flexible wall foil members 404, 405 sealed together at the periphery thereof by welded seams 406, thereby forming a relatively flat pouch for containing the liquid drug, the welded seam of the pouch defining a general plane. An elastomeric septum member 410 is mounted on the first foil member, preferably by welding. The septum member comprises a relatively thin disc-formed base portion from the central portion of which projects an extension 411, the peripheral circumferential part 412 of the base portion forming a needle-penetratable self-sealing connection means. The projection may be utilized e.g. during manufacture and handling of the reservoir, as well as a mounting means for fixating the reservoir relative to other structures without having to interfere with movement of the flexible foil walls.

Figure 7A:
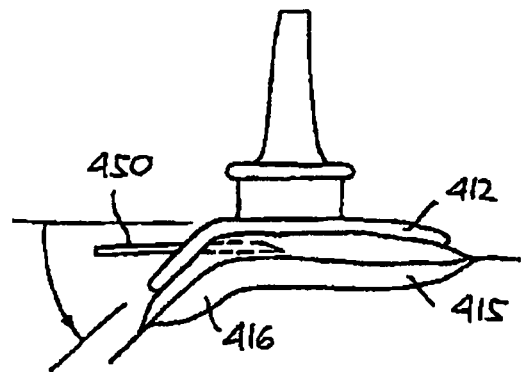
FIG. 7A shows a side view of a reservoir with a needle inserted.
Figure 7B:
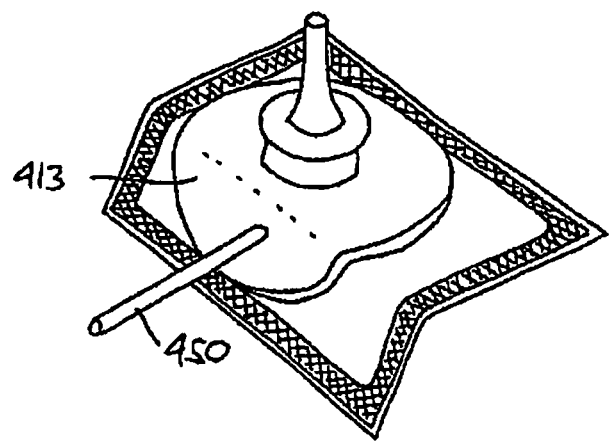
FIG. 7B shows an upper perspective view of the reservoir of FIG. 7A.
Figure 7C:
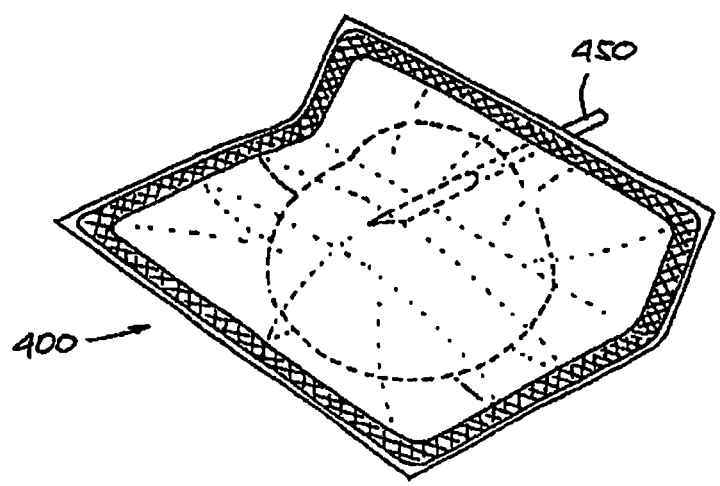
FIG. 7C shows a lower perspective view of the reservoir of FIG. 7A.

Although the filled reservoir 400 comprises a generally convex first surface allowing a needle to be inserted therethrough generally in parallel with the general plane of the reservoir, FIG. 7A-C shows an arrangement of the reservoir allowing for improved insertion of a needle through the needle-penetratable portion 412 of the septum in parallel with the general plane of the reservoir.

More specifically, by deflecting a portion of the reservoir downwardly relative to the general plane (by e.g. approximately 30 degrees as shown in FIG. 7A), an area 413 of the needle-penetratable portion of the septum is "presented" to a needle 450 arranged in parallel with the general plane of the reservoir, thereby allowing for ease of insertion. As shown in FIG. 7A, the bend reservoir comprises a first "major" portion 415 being arranged substantially corresponding to the general plane, and a second "minor" portion 416 being deflected relative thereto in a direction away from the first surface, such that a part 413 of the peripheral portion of the septum member is arranged on the second portion of the reservoir. In FIGS. 7A-7C the reservoir is shown without the means for bending the reservoir, however, such means can be provided by structures of a surrounding housing. The needle 450 may be in the form of a moveable needle connector as described above.

Example: A reservoir containing 3 ml of insulin was manufactured from two foil members of a three-layered laminate comprising an intermediate layer of PCTFE co-extruded with epoxy modified polyethylene imine (a tie-layer) and an inner layer of PE, and with an outer layer of PP laminated on the PCTFE layer. A septum member made from a thermoplastic elastomeric rubber-compound was welded to the outer PP layer before the two foil members were welded to each other along the peripheries thereof, the insulin being filled into the reservoir before it was completely sealed.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An apparatus for dispensing medical fluids comprising:
a housing,
a flexible reservoir containing a medical fluid and comprising first and second flexible foil portions sealed together to form an enclosed cavity for containing the medical fluid, the reservoir having a pouch-like configuration and having a rounded, folded peripheral edge formed from the first and second flexible foil portions, the flexible reservoir comprising a self-sealing septum member formed from a needle-penetratable flexible material, at least a portion of the flexible reservoir being arranged within the housing,
the septum member being attached to the flexible foil corresponding to the rounded, folded peripheral edge, and
a mount arranged within or formed by the housing, the mount being configured to directly engage the septum member to secure the flexible reservoir relative to the mount.

2. An apparatus as in claim 1, wherein at least a portion of the flexible reservoir apart from the septum member is free to move relative to the mount.

3. An apparatus as in claim 1, further comprising:
a fluid conduit having an inlet and an outlet, the inlet being adapted to be arranged in fluid communication with the reservoir through the septum member,
wherein the fluid conduit and the reservoir are moveable relative to each other from an initial position in which there is no fluid communication therebetween and a connected position in which the fluid conduit inlet is arranged in fluid communication with the reservoir through the septum member.

4. An apparatus as in claim 3, wherein the inlet of the fluid conduit is in the form of a pointed needle portion.

5. An apparatus as in claim 4, wherein the septum member has been mounted on an outer surface portion of the reservoir by means of welding.

6. An apparatus as in claim 1, further comprising an expelling assembly adapted to expel a fluid contained in the reservoir through a fluid communication made in the septum member.

7. An apparatus as in claim 1, further comprising an expelling assembly having an inlet and an outlet and an internal flow path arranged therebetween, the inlet being adapted to be arranged in fluid communication with the reservoir, the expelling assembly being adapted to expel a fluid contained in the reservoir through the outlet of the expelling assembly.

8. An apparatus as in claim 7, wherein the expelling assembly comprises a fluid connector serving as the inlet for the expelling assembly,
wherein the fluid connector is arranged within the interior of the expelling assembly in an initial state, the fluid connector comprising an inlet and an outlet, whereby the fluid connector is arranged to be operated from the initial state and to an operating state in which fluid communication is established between the interior of the reservoir and the interior of the expelling assembly via the fluid connector and with the outlet of the fluid connector being arranged in the flow path of the expelling assembly.

9. An apparatus as in claim 1, wherein the septum member is disc shaped.

* * * * *